United States Patent
Liao et al.

(10) Patent No.: US 9,669,402 B2
(45) Date of Patent: Jun. 6, 2017

(54) ANIONIC EXCHANGE-HYDROPHOBIC MIXED MODE

(71) Applicants: Jiali Liao, San Ramon, CA (US); Russell Frost, Concord, CA (US)

(72) Inventors: Jiali Liao, San Ramon, CA (US); Russell Frost, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 89 days.

(21) Appl. No.: 13/785,632

(22) Filed: Mar. 5, 2013

(65) Prior Publication Data

US 2013/0237692 A1    Sep. 12, 2013

Related U.S. Application Data

(60) Provisional application No. 61/608,418, filed on Mar. 8, 2012.

(51) Int. Cl.

| | |
|---|---|
| *B01D 15/26* | (2006.01) |
| *C07K 1/14* | (2006.01) |
| *B01J 20/281* | (2006.01) |
| *B01J 41/20* | (2006.01) |
| *C07K 1/16* | (2006.01) |
| *B01D 15/30* | (2006.01) |
| *B01D 15/32* | (2006.01) |
| *B01D 15/36* | (2006.01) |
| *B01D 15/38* | (2006.01) |
| *B01J 20/286* | (2006.01) |
| *B01J 20/289* | (2006.01) |
| *B01J 20/32* | (2006.01) |

(52) U.S. Cl.
CPC .......... *B01J 41/20* (2013.01); *B01D 15/265* (2013.01); *B01D 15/30* (2013.01); *B01D 15/327* (2013.01); *B01D 15/363* (2013.01); *B01D 15/3847* (2013.01); *B01J 20/281* (2013.01); *B01J 20/286* (2013.01); *B01J 20/289* (2013.01); *B01J 20/3253* (2013.01); *C07K 1/14* (2013.01); *C07K 1/16* (2013.01); *C07K 1/165* (2013.01); *G01N 30/482* (2013.01)

(58) Field of Classification Search
None
See application file for complete search history.

(56) References Cited

U.S. PATENT DOCUMENTS

| | | | |
|---|---|---|---|
| 4,415,631 A * | 11/1983 | Schutijser | ............ 428/405 |
| 5,225,483 A * | 7/1993 | Datta et al. | ............ 525/73 |
| 6,702,943 B1 | 3/2004 | Johansson et al. | |
| 6,783,929 B1 | 8/2004 | Zuckermann et al. | |
| 7,867,784 B2 | 1/2011 | Engstrand et al. | |
| 8,021,889 B2 | 9/2011 | Boschetti et al. | |
| 2006/0135355 A1 | 6/2006 | Hems et al. | |
| 2010/0181254 A1 * | 7/2010 | Graalfs | ........ B01D 15/362 210/656 |
| 2011/0118442 A1 | 5/2011 | Engstrand et al. | |

FOREIGN PATENT DOCUMENTS

| | | | | |
|---|---|---|---|---|
| SE | WO 9729825 A1 | * | 8/1997 | ...... B01D 15/363 |
| WO | 02/070124 A1 | | 9/2002 | |
| WO | 03/097693 A1 | | 11/2003 | |
| WO | 2006/001771 A1 | | 1/2006 | |
| WO | WO 2010117598 A2 | * | 10/2010 | |
| WO | 2011/044637 A1 | | 4/2011 | |

OTHER PUBLICATIONS

Chen, S., Lau, H., Brodsky, Y., Kleemann, G., Latypov, R. The use of native cation-exchange chromatography to study aggregation and phase separation of monoclonal antibodies. Protein Science. Volumn 19, Issue 6, pp. 1191-1204. Apr. 13, 2010.*
UC Davis. Wandall, A. Chemistry of Nitrogen. Accessed on Feb. 19, 2015 from <http://chemwiki.ucdavis.edu/Inorganix Chemistry . . . >.*
Sakurai, K; Goto, Y. Manipulating Monomer-Dimer Equilibrium of Bovine B-lactoglobulin by Amino Acid Substitution. The Journal of Biological Chemistry. vol. 277, No. 28, Issue of Jul. 12, pp. 25735-25740, 2002.*
Sakurai, K. Motohisa, O. Goto, Y. Salt-dependent monomer-dimer equilibrium of bovine B-lactoglobulin at pH 3. Protein Sci. Nov. 2001; 10(11): 2325-2335.*
International Search Report and Written Opinion from PCT/US2013/029097, dated May 13, 2013.
Peng et al., "Preparation of phenothiazine bonded silica gel as sorbents of solid phase extraction and their application for determination of nitrobenzene compounds in environmental water by gas chromatography-mass spectrometry," *J. Chromatogr. A*, 1218(52):9314-9320 (Oct. 25, 2011).
Tishchenko et al. "Purification of the specific immunoglobulin $G_1$ by immobilized metal ion affinity chromatography using nickel complexes of chelating porous and nonporous polymeric sorbents based on poly(methacrylic esters)—Effect of polymer structure," *J. Chromatogr. A*, 954(1-2):115-126 (Apr. 19, 2002).

(Continued)

*Primary Examiner* — Katherine Zalasky
*Assistant Examiner* — Kara Graber
(74) *Attorney, Agent, or Firm* — Kilpatrick Townsend & Stockton LLP

(57) ABSTRACT

Solid supports and ligands are provided for purification of biomolecules by mixed-mode anion exchange-hydrophobic chromatography. Compositions can have the formula Support-(X)—N($R^1$, $R^2$)—$R^3$-L-Ar, or a salt thereof, wherein: Support is a chromatographic solid support; X is a spacer or absent; $R^1$ and $R^2$ are each selected from hydrogen and an alkyl comprising 1-6 carbons; $R^3$ is an alkyl comprising 1-6 carbons or a cyclo alkyl comprising 1-6 carbons; L is $NR^4$, O, or S; wherein $R^4$ is hydrogen or an alkyl comprising 1-6 carbons; and Ar is an aryl. Methods are also provided for using solid supports and ligands to purify biomolecules such as monomeric antibodies.

21 Claims, No Drawings

(56) References Cited

OTHER PUBLICATIONS

Extended European Search Report from EP Appl. No. 13758660.8, dated Jun. 30, 2016.

* cited by examiner

ANIONIC EXCHANGE-HYDROPHOBIC MIXED MODE

CROSS-REFERENCE TO RELATED PATENT APPLICATIONS

The present application claims benefit of priority to U.S. Provisional Patent Application No. 61/608,418, filed Mar. 8, 2012, which is incorporated by reference for all purposes.

BACKGROUND OF THE INVENTION

The extraction of immunoglobulins from source liquids, which are primarily mammalian bodily fluids or cell culture harvest, is of value in obtaining the immunoglobulins in a sufficiently concentrated or purified form for diagnostic and therapeutic uses as well as laboratory studies in general. Similarly, purification of other types of proteins and other molecules from biological samples can be of value.

BRIEF SUMMARY OF THE INVENTION

Chromatographic solid supports (Support) linked to a ligand are provided. In some embodiments, the support and ligand have the formula:
Support-(X)—N($R^1$, $R^2$)—$R^3$-L-Ar wherein, X is a spacer or absent; $R^1$ and $R^2$ are each selected from hydrogen and an alkyl comprising 1-6 carbons; $R^3$ is an alkyl comprising 1-6 carbons or a cyclo alkyl comprising 1-6 carbons; L is $NR^4$, O, or S; wherein $R^4$ is hydrogen or an alkyl comprising 1-6 carbons; and Ar is an aryl.

In some embodiments, $R^1$ and $R^2$ are hydrogen.

In some embodiments, $R^3$ is an alkyl comprising 1-4 carbons.

In some embodiments, $R^3$ is an alkyl comprising 1, 2, 3, 4, 5, or 6 carbons.

In some embodiments, the aryl is a phenyl. In some embodiments, the aryl is a substituted phenyl. In some embodiments, the substituted phenyl is an alkyl-substituted phenyl.

In some embodiments, $R^1$ and/or $R^2$ are an alkyl comprising 1-6 carbons and Ar is an alkyl-substituted phenyl.

In some embodiments, the ligand is N-phenylethylenediamine or a salt thereof. In some embodiments, the ligand is 2-phenoxyethylamine or a salt thereof.

In some embodiments, X (linker/spacer) is absent. In some embodiments, X is a spacer.

Also provided are methods of purifying a biomolecule from a sample. In some embodiments, the method comprises contacting the sample to the chromatographic solid support linked to the ligand as described above or elsewhere herein; and collecting a purified biomolecule.

In some embodiments, the biomolecule is a protein. In some embodiments, the protein is an antibody.

In some embodiments, the sample comprises monomeric antibodies and aggregates, and monomeric antibodies are separated from the aggregates, thereby resulting in purification of monomeric antibodies.

In some embodiments, the purified biomolecule is a monomeric antibody. In some embodiments, monomeric antibodies of the sample are immobilized on the chromatographic solid support and subsequently eluted. In some embodiments, monomeric antibodies of the sample flow past the chromatographic solid support and are collected.

DEFINITIONS

"Antibody" refers to an immunoglobulin, composite (e.g., fusion), or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc, whether or not they retain antigen-binding function.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

As used herein, the term "cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$ cycloalkyl includes cyclopropyl, cyclobutyl, cyclopentyl, cyclohexyl, cyclooctyl, and norbornane.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Examples of substituted phenyl groups are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "linker" or "spacer" refers to a chemical moiety that links the chromatographic ligand of the present invention to the chromatographic matrix. Linkers useful in the present invention can be, for example, up to 30 carbon atoms in length. The types of bonds used to link the linker to the compound and biological molecule of the present invention include, but are not limited to, amides, amines, esters, carbamates, ureas, thioethers, thiocarbamates, thiocarbonate and thioureas. One of skill in the art will appreciate that other types of bonds are useful in the present invention. As noted elsewhere herein, the inclusion of a spacer between the ligand and the solid support matrix is optional.

"Biomolecule preparation" and "biological sample" refer to any composition containing a target molecule of biological origin (a "biomolecule") that is desired to be purified. In some embodiments, the target molecule to be purified is an antibody or non-antibody protein.

"Bind-elute mode" refers to an operational approach to chromatography in which the buffer conditions are established so that target molecules and, optionally undesired contaminants, bind to the ligand when the sample is applied to the ligand (which is optionally bound to a solid support). Fractionation of the target can be achieved subsequently by changing the conditions such that the target is eluted from the support. In some embodiments, contaminants remain bound following target elution. In some embodiments, contaminants either flow-through or are bound and eluted before elution of the target.

"Flow-through mode" refers to an operational approach to chromatography in which the buffer conditions are established so that the target molecule to be purified flows through the chromatography support comprising the ligand, while at least some sample contaminants are selectively retained, thus achieving their removal.

DETAILED DESCRIPTION OF THE INVENTION

I. Introduction

Described herein are a class of chromatography ligands that allow for efficient purification of target biomolecules from a sample, and that has been found to be particularly useful in purifying monomeric target biomolecules from aggregate target biomolecules. Notably, the examples demonstrate that ligands described herein are superior for separating monomeric antibodies from antibody aggregates than the commercial product, CAPTO® Adhere (ligand: N-benzyl-N-methyl ethanolamine).

II. Chromatography Ligands

The chromatographic ligands described herein can, in some embodiments, be represented by the formula:

—N(R$^1$,R$^2$)—R$^3$-L-Ar, or a salt thereof wherein

R$^1$ and R$^2$ are each selected from hydrogen and an alkyl;
R$^3$ is an alkyl or a cyclo alkyl;
L is NR$^4$, O, or S; wherein R$^4$ is hydrogen or an alkyl; and
Ar is an aryl.

The nitrogen of the N(R$^1$, R$^2$) can be a secondary, tertiary or quaternary amine. The positively-charged (salt) form of this nitrogen can play a role in binding of target biomolecules (e.g., in anion exchange) and thus, in purification methods the ligand will often be used under conditions such that the nitrogen is positively charged for at least part of target binding to the ligand, washing, or elution.

In a number of embodiments, R$^1$ and R$^2$ are hydrogens. The examples include several embodiments in which R$^1$ and R$^2$ are hydrogens, showing superior purification of monomeric targets.

Alternatively, in some embodiments, R$^1$, R$^2$, or both, are an alkyl (e.g., including but not limited to a linear C1, C2, C3, C4, or C5 alkyl). An embodiment comprising methyl (C1) at R$^1$ and Ar being phenyl did not significantly bind monoclonal antibodies under conditions having 300 mM NaCl. However, without being bound to a particular theory of action, it is believed that antibody binding to ligands having R$^1$ or R$^2$ alkyls can be improved by an using alkyl-substituted aryl at the "Ar" position of the ligand in combination with R$^1$ or R$^2$ alkyls.

R$^3$ can be an alkyl or a cyclo alkyl. In some embodiments, R$^3$ is a linear alkyl having 1, 2, 3, 4, 5, or 6 carbons. For example, in phenylethylenediamine and pheoxythylamine, R$^3$ is a two-carbon alkyl.

The moiety "L" can be oxygen (e.g., as an ether), sulfur (e.g., as a thioether) or NR$^4$, e.g., NH or where NR$^4$ is an alkyl (e.g., including but not limited to linear C1, C2, C3, C4, or C5 alkyl).

The aryl group will generally be a phenyl. However, in some embodiments, the aryl is a substituted aryl, e.g., substituted with one or more alkyl moieties (e.g., including but not limited to linear C1, C2, C3, C4, or C5 alkyl). In some embodiments, R$^1$, R$^2$, or both, are an alkyl and the aryl is a substituted (e.g., alkyl-substituted) aryl, such as an alkyl-substituted phenyl.

The ligands can be linked to a solid support (S), optionally via a spacer (X) as follows:

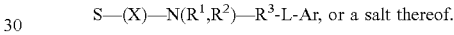
S—(X)—N(R$^1$,R$^2$)—R$^3$-L-Ar, or a salt thereof.

Any solid support is contemplated for linkage to the ligands. The solid support can be, for example, porous or non-porous and can be in the form, for example, of a matrix, bead, particle, chip, or other conformation, e.g., a membrane or a monolith, i.e., a single block, pellet, or slab of material. Particles when used as matrices can be spheres or beads, either smooth-surfaced or with a rough or textured surface. Many, and in some cases all, of the pores are through-pores, extending through the particles to serve as channels large enough to permit hydrodynamic flow or fast diffusion through the pores. When in the form of spheres or beads, the median particle diameter, where the term "diameter" refers to the longest exterior dimension of the particle, is in some embodiments within the range of about 25 microns to about 150 microns. Disclosures of matrices meeting the descriptions in this paragraph and the processes by which they are made are found in Hjertén et al., U.S. Pat. No. 5,645,717, Liao et al., U.S. Pat. No. 5,647,979, Liao et al., U.S. Pat. No. 5,935,429, and Liao et al., U.S. Pat. No. 6,423,666. Examples of monomers that can be polymerized to achieve useful matrices are vinyl acetate, vinyl propylamine, acrylic acid, methacrylate, butyl acrylate, acrylamide, methacrylamide, vinyl pyrrolidone (vinyl pyrrolidinone), with functional groups in some cases. Cross-linking agents are also of use in many embodiments, and when present can in some embodiments constitute a mole ratio of from about 0.1 to about 0.7 relative to total monomer. Examples of crosslinking agents are dihydroxyethylenebisacrylamide, diallyltartardiamide, triallyl citric triamide, ethylene diacrylate, bisacrylylcystamine, N,N'-methylenebisacrylamide, and piperazine diacrylamide.

As noted above, the ligands can be linked directly (without a spacer) to the solid support or via a linker. Linkage to the solid support will depend on the specific solid support used. In some embodiments, the solid support comprises a diol, which is converted to an aldehyde, e.g., by conversion with NaIO$_4$. The amine of the ligand can be linked to an aldehyde on the solid support by a reductive amination reaction, thereby directly coupling the ligand to the solid support.

In some embodiments, the ligand is linked to the solid support via a spacer. The spacer may be introduced according to conventional covalent coupling methodologies. Exemplary coupling chemistries can involve, for example, epichlorohydrin, epibromohydrin, allyl-glycidylether, bisepoxides such as butanedioldiglycidylether, halogen-substituted aliphatic substances such as di-chloro-propanol, divinyl sulfone, carbonyldiimidazole, aldehydes such as glutaric dialdehyde, quinones, cyanogen bromide, periodates such as sodium-meta periodate, carbodiimides, chloro-triazines, sulfonyl chlorides such as tosyl chlorides and tresyl chlorides, N-hydroxy succinimides, oxazolones, maleimides, 2-fluoro-1-methylpyridinium toluene-4-sulfonates, pyridyl disulfides and hydrazides.

The solid support can be utilized in any conventional configuration, including packed columns and fluidized or expanded-bed columns, monoliths or porous membranes, and by any conventional method, including batchwise modes for loading, washes, and elution, as well as continuous or flow-through modes. In some embodiments, a column can range in diameter from 1 cm to 1 m, and in height from 1 cm to 30 cm or more.

III. Methods

Also provided are methods of purifying one or more target biomolecules from a sample comprising applying the sample to the ligand linked to a solid support and subsequently collecting the target biomolecules from the solid support, thereby purifying the target biomolecules from one or more component in the sample. As noted above, in some embodiments, the target biomolecule is a monomeric antibody and the method comprises purifying the monomeric antibody from aggregated antibodies in the sample.

The chromatographic ligands are useful for purifying target molecules using anionic exchange (i.e., where the ligand is positively charged) and hydrophobic mixed mode chromatography. The conditions can be adjusted so as to run the chromatography in bind-elute mode or flow-through mode.

Protein preparations to which the methods can be applied may include unpurified or partially purified antibodies (e.g. IgG) from natural, synthetic, or recombinant sources. Unpurified antibody preparations, for example, may come from various sources including, but not limited to, plasma, serum, ascites fluid, milk, plant extracts, bacterial lysates, yeast lysates, or conditioned cell culture media. Partially purified protein preparations may come from unpurified preparations that have been processed by at least one chromatography, precipitation, other fractionation step, or any combination of the foregoing. The chromatography step or steps may employ any method, including but not limited to size exclusion, affinity, anion exchange, cation exchange, protein A affinity, hydrophobic interaction, immobilized metal affinity chromatography, or hydroxyapatite chromatography. The precipitation step or steps may include salt or polyethylene glycol (PEG) precipitation, or precipitation with organic acids, organic bases, or other agents. Other fractionation steps may include but are not limited to crystallization, liquid:liquid partitioning, or membrane filtration.

As will be appreciated in the art, load, wash and elution conditions for use in the mixed mode chromatography will depend on the specific chromatography media/ligands used.

In some bind-elute mode embodiments, loading (i.e., binding the antibodies to the matrix), and optionally washing, is performed at a pH above 7, e.g., between 7-8, 7-9, etc. Some exemplary bind-elute conditions are:

binding condition: 100-300 mM NaCl, pH 6.5-8.5 in a buffer (e.g., Tris or phosphate);

elution condition: 0-150 mM NaCl, pH 4.0-6.0, using sodium acetate buffer.

Optionally, the matrix can be washed under conditions such that some components of the sample are removed from the solid support but the target biomolecules remain immobilized on the matrix. In some embodiments, the target biomolecule is subsequently eluted by lowering the salt concentration and/or reducing the pH of the solution in contact with the matrix.

Alternatively, the sample can be applied in flow through mode in which some components of the sample are immobilized to the matrix but the target biomolecules flow through (i.e., flow passed) the solid support, and is collected. Some exemplary flow through conditions are 0-150 mM NaCl, pH 4.0-8.0; appropriate buffers can include, e.g., 2-(N-morpholino)ethanesulfonic acid (MES), Bis-Tris, sodium acetate or citrate-phosphate.

EXAMPLE

Example 1: Generation of Matrix Comprising N-phenylethylendiamine

UNOSPHERE® Diol (20 mL), a copolymer of 3-allyloxy-1,2-propanediol and vinyl pyrrolidinone, crosslinked with N,N'-methylenebisacrylamide and with a diol density of 200-300 µmol/mL, was used in the form of spherical beads. The beads were suspended in 20 mL of either 0.1M sodium acetate or water. Sodium periodate was added to a concentration within the range of 50 to 100 mM, and the resulting mixture was incubated at room temperature (approximately 70° F. (21° C.)) for 3-24 hours. The reaction resulted in conversion of the diol groups to aldehyde groups in the range of 150-250 µmol/mL. The resulting aldehyde-functionalized resin was transferred to a 20-mL column where it was washed with 100 mL of water.

Twenty milliliters of UNOSPHERE® aldehyde resin was then suspended in 20 ml of 0.20M sodium phosphate containing 0.6 g of N-phenylethylenediamine at pH 7.0. After this mixture was incubated (shaking, 200 rpm) at room temperature for 15 minutes, 200 mg NaBH$_3$CN was then added and the reaction was allowed to continue for 3-20 hours. The N-phenylethylenediamine concentration in the reaction was determined to be in the range of 25-200 mM. At the end of the reaction, resin was transferred to a 20 ml column, washed with 3 CV of water followed by 1-2 CV of 0.1N HCl, and then washed with 5 CV water. The N-phenylethylenediamine ligand density was in the range of 25-100 µmol/ml.

Example 2: Use of Matrix Comprising N-phenylethylendiamine: pH 8.5-4.5 Gradient

The resin with the N-phenylethylenediamine ligand (generated as described above) was packed into a 7 mm (i.d.)×5.5 cm column and equilibrated with 20 mM Tris-HCl buffer containing 300 mM NaCl, pH 8.5. 500 µl of 6.0 mg/ml solution of a monoclonal IgG antibody containing 5-10% aggregated antibodies, was applied to the column at a flow rate of 2 ml/minute. The antibody was eluted in a 10 ml gradient for equilibration buffer to elution buffer of 20 mM sodium acetate containing 150 mM NaCl at pH 4.5, followed with 30 ml isocratic elution with elution buffer. The collected antibody elution fractions were analyzed by size exclusion high performance liquid chromatography (HPLC-SEC) to determine the content of aggregated antibody in the elution fractions. No antibody aggregates were detected in the antibody elution fractions.

A similar experiment was performed using a CAPTO® Adhere (ligand: N-benzyl-N-methyl ethanolamine) column. Aggregated antibody species were found in all fractions derived from the CAPTO® Adhere column.

Example 3: Use of Matrix Comprising N-phenylethylendiamine: pH 7.0-4.5 Gradient A similar experiment to the one described above was conducted using an equilibration buffer at pH 7.0 with 20 mM sodium phosphate buffer containing 300 mM NaCl. No aggregated antibody was detected in the monoclonal antibody fractions.

A similar experiment was performed using a CAPTO® Adhere (ligand: N-benzyl-N-methyl ethanolamine) column. Aggregated antibody species were found in fractions derived from the CAPTO® Adhere column.

Example 4: Generation of Matrix Comprising 2-phenoxyethylamine

A matrix comprising the ligand 2-phenoxyethylamine was generated using reaction conditions as provided in Example 1, replacing N-phenylethylenediamine with 2-phenoxyethylamine. 2-phenoxyethylamine ligand density was ~49 µmol/ml.

Example 5: Use of Matrix Comprising 2-phenoxyethylamine: pH 7.0-4.5

A matrix comprising the ligand 2-phenoxyethylamine was used to purify antibodies similar to the method described in Example 2.

The resin with the 2-phenoxyethylamine ligand was packed into a 7 mm (i.d.)×5.5 cm column and equilibrated with 20 mM sodium phosphate buffer containing 300 mM NaCl, pH 7.0. 500 µl of 6.0 mg/ml solution of a monoclonal IgG antibody containing 5-10% aggregated antibodies, was applied to the column at a flow rate of 2 ml/minute. The antibody was eluted in a 10 ml gradient for equilibration buffer to elution buffer of 20 mM sodium acetate containing 150 mM NaCl at pH 4.5, followed with 30 ml isocratic elution with elution buffer. The collected antibody elution fractions were analyzed by size exclusion high performance liquid chromatography (HPLC-SEC) to determine the content of aggregated antibody in the elution fractions. No antibody aggregates were detected in the antibody elution fractions.

Example 6: Use of Matrix Comprising 2-phenoxyethylamine: pH 4.5 flow-through Mode A matrix comprising the ligand 2-phenoxyethylamine was used to purify antibodies similar to the method described in Example 2, except that the antibody sample was applied to the column using an equilibration buffer at pH 4.5.

The resin with the 2-phenoxyethylamine ligand was packed into a 7 mm (i.d.)×5.5 cm column and equilibrated with 20 mM sodium acetate containing 75 mM NaCl at pH 4.5. 750 µl of 2.0 mg/ml solution of a monoclonal IgG antibody containing 15-20% aggregated antibodies, was applied to the column at a flow rate of 2 ml/minute. The antibody flowed through the column. The column was washed in a 10 ml gradient for equilibration buffer to elution buffer of 20 mM sodium acetate at pH 4.5, followed with 10 ml isocratic elution with elution buffer. The collected antibody in the flow-through fractions was analyzed by size exclusion high performance liquid chromatography (HPLC-SEC) to determine the content of aggregated antibody. No antibody aggregates were detected in the antibody flow-through fractions.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

What is claimed is:

1. A method of purifying a biomolecule from a sample, the method comprising
contacting the sample to a chromatographic solid support linked to a ligand according to formula (I):

$$\text{Support-(X)}\!\!-\!\!\text{N}(R^1,R^2)\!\!-\!\!R^3\text{-L-Ar, or a salt thereof} \qquad (I),$$

wherein
X is a spacer or absent;
$R^1$ and $R^2$ are each selected from hydrogen and an alkyl comprising 1-6 carbons;
$R^3$ is an alkyl comprising 1-6 carbons or a cyclo alkyl comprising 1-6 carbons;
L is $NR^4$, O, or S; wherein $R^4$ is hydrogen or an alkyl comprising 1-6 carbons;
Ar is an aryl; and
the nitrogen in the $N(R^1, R^2)$ is positively charged during the contacting; and
collecting a purified biomolecule.

2. The method of claim 1, wherein the purified biomolecule is a protein.

3. The method of claim 2, wherein the protein is an antibody.

4. The method of claim 1, wherein the sample comprises a monomeric antibody and antibody aggregates, the purified biomolecule comprises the monomeric antibody, and the method comprises separating the monomeric antibody from the antibody aggregates.

5. The method of claim 1, wherein the purified biomolecule is a monomeric antibody.

6. The method of claim 5, wherein the monomeric antibody is immobilized on the chromatographic solid support and subsequently eluted.

7. The method of claim 5, wherein the purification operates in flow-through mode, and the monomeric antibody flows past, without binding to, the chromatographic solid support, and is collected.

8. The method of claim 5, wherein $R^1$ and $R^2$ are hydrogen.

9. The method of claim 5, wherein $R^3$ is an alkyl comprising 1-4 carbons.

10. The method of claim 5, wherein $R^3$ is an alkyl comprising 2 carbons.

11. The method of claim 5, wherein the aryl is a phenyl.

12. The method of claim 5, wherein the aryl is a substituted phenyl.

13. The method of claim 12, wherein the substituted phenyl is an alkyl-substituted phenyl.

14. The method of claim 5, wherein $R^1$ and/or $R^2$ are an alkyl comprising 1-6 carbons and Ar is an alkyl-substituted phenyl.

15. The method of claim 5, wherein the ligand is N-phenylethylenediamine or a salt thereof.

16. The method of claim 5, wherein the ligand is 2-phenoxyethylamine or a salt thereof.

17. The method of claim 5, wherein X is absent.

18. The method of claim 5, wherein X is a spacer.

19. The method of claim 18, wherein the spacer is up to 30 carbon atoms in length.

20. The method of claim 5, wherein the purification operates in bind-elute mode.

21. The method of claim 20, wherein the biomolecule is eluted by a step comprising reduction of pH of solution in contact with the ligand.

* * * * *